US009931252B2

(12) United States Patent
Carney et al.

(10) Patent No.: US 9,931,252 B2
(45) Date of Patent: Apr. 3, 2018

(54) METHOD AND COMPUTER PROGRAM FOR MONITORING USE OF AN ABSORBENT PRODUCT

(75) Inventors: Joshua Carney, Mölndal (SE); Henrik Carlén, Västra Frölunda (SE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 0 days.

(21) Appl. No.: 14/361,494

(22) PCT Filed: Dec. 21, 2011

(86) PCT No.: PCT/SE2011/051566
§ 371 (c)(1),
(2), (4) Date: May 29, 2014

(87) PCT Pub. No.: WO2013/095231
PCT Pub. Date: Jun. 27, 2013

(65) Prior Publication Data
US 2014/0292520 A1    Oct. 2, 2014

(51) Int. Cl.
*G08B 23/00* (2006.01)
*A61F 13/42* (2006.01)
(Continued)

(52) U.S. Cl.
CPC ............ *A61F 13/42* (2013.01); *G06F 19/345* (2013.01); *G06F 19/3418* (2013.01); *G08B 21/20* (2013.01); *A61F 2013/424* (2013.01)

(58) Field of Classification Search
CPC ............... A61F 13/42; A61F 2013/424; G06F 19/3418; G06F 19/345; G08B 21/20
See application file for complete search history.

(56) References Cited

U.S. PATENT DOCUMENTS 4,834,733 A    5/1989  Huntoon
5,144,284 A    9/1992  Hammett
(Continued)

FOREIGN PATENT DOCUMENTS

CN    101472543 A    7/2009
CN    102076298 A    5/2011
(Continued)

OTHER PUBLICATIONS

The Journal of Urology, Complications of Mesh-Augmented Pelvic Organ Prolapse and Incontinence Repairs—Case Series of 319 Procedures, May 22, 2012, pp. e626-e628.*
(Continued)

*Primary Examiner* — Quang D Pham
(74) *Attorney, Agent, or Firm* — Buchanan Ingersoll & Rooney PC

(57) ABSTRACT

A method for monitoring use of an absorbent product, such as an incontinence pad or a diaper, worn by a wearer is provided. The method includes obtaining, by way of a mobile device, intake information indicative of intake of fluid and/or solid material by the wearer, obtaining, by way of the mobile device, voiding information indicative of urinary and/or faecal voiding by the wearer, predicting, based on the intake and voiding information, future voiding by the wearer, and providing, by way of the mobile device, product-related information based on the prediction. In this way, the product-wearer or his caregiver can be provided with valuable information related to the use of the product, for example recommendations on when to change the product.

15 Claims, 3 Drawing Sheets

(51) Int. Cl.
   *G06F 19/00* (2018.01)
   *G08B 21/20* (2006.01)

(56) References Cited

U.S. PATENT DOCUMENTS

| | | | |
|---|---|---|---|
| 5,416,469 A * | 5/1995 | Colling | 340/573.5 |
| 5,691,932 A | 11/1997 | Reiner et al. | |
| 5,709,222 A | 1/1998 | Davallou | |
| 5,978,712 A | 11/1999 | Suda et al. | |
| 6,266,557 B1 * | 7/2001 | Roe et al. | 600/546 |
| 6,354,991 B1 | 3/2002 | Gross et al. | |
| 6,544,173 B2 | 4/2003 | West et al. | |
| 6,617,488 B1 | 9/2003 | Springer et al. | |
| 6,652,449 B1 | 11/2003 | Gross et al. | |
| 7,250,547 B1 | 7/2007 | Hofmeister et al. | |
| 7,399,276 B1 | 7/2008 | Brown et al. | |
| 7,700,821 B2 | 4/2010 | Ales, III et al. | |
| 7,737,322 B2 | 6/2010 | Ales, III et al. | |
| 7,800,505 B2 | 9/2010 | Pietersen | |
| 7,855,653 B2 | 12/2010 | Rondoni et al. | |
| 7,977,529 B2 | 7/2011 | Bergman et al. | |
| 8,121,691 B2 | 2/2012 | Gerber et al. | |
| 8,196,809 B2 | 6/2012 | Thorstensson | |
| 8,395,014 B2 | 3/2013 | Helmer et al. | |
| 9,020,572 B2 * | 4/2015 | Mensinger | A61B 5/7445 600/345 |
| 9,317,913 B2 | 4/2016 | Carney | |
| 9,402,771 B2 | 8/2016 | Carney et al. | |
| 2001/0039503 A1 | 11/2001 | Chan et al. | |
| 2002/0026164 A1 | 2/2002 | Camarero Roy et al. | |
| 2002/0145526 A1 | 10/2002 | Friedman et al. | |
| 2003/0078553 A1 | 4/2003 | Wada et al. | |
| 2003/0171791 A1 * | 9/2003 | KenKnight | A61N 1/36514 607/60 |
| 2004/0055367 A1 * | 3/2004 | Swiecicki | A61F 13/42 73/73 |
| 2004/0078014 A1 | 4/2004 | Shapira | |
| 2004/0100376 A1 | 5/2004 | Lye et al. | |
| 2004/0220538 A1 | 11/2004 | Panopoulos | |
| 2004/0230172 A1 | 11/2004 | Shapira | |
| 2005/0033250 A1 | 2/2005 | Collette et al. | |
| 2005/0137542 A1 | 6/2005 | Underhill et al. | |
| 2005/0195085 A1 | 9/2005 | Cretu-Petra | |
| 2005/0245839 A1 | 11/2005 | Stivoric et al. | |
| 2006/0064037 A1 | 3/2006 | Shalon et al. | |
| 2007/0142799 A1 | 6/2007 | Ales et al. | |
| 2007/0156504 A1 * | 7/2007 | Myers | A61F 13/84 705/2 |
| 2007/0252713 A1 | 11/2007 | Rondoni et al. | |
| 2007/0252714 A1 | 11/2007 | Rondoni et al. | |
| 2007/0255176 A1 | 11/2007 | Rondoni et al. | |
| 2007/0270774 A1 | 11/2007 | Bergman et al. | |
| 2008/0046292 A1 | 2/2008 | Myers et al. | |
| 2008/0052030 A1 | 2/2008 | Olson et al. | |
| 2008/0058740 A1 | 3/2008 | Sullivan et al. | |
| 2008/0074274 A1 | 3/2008 | Hu et al. | |
| 2008/0104104 A1 | 5/2008 | Nolan et al. | |
| 2008/0104615 A1 | 5/2008 | Nolan et al. | |
| 2008/0167535 A1 | 7/2008 | Stivoric et al. | |
| 2008/0266617 A1 | 10/2008 | Song et al. | |
| 2008/0300470 A1 | 12/2008 | Gerber et al. | |
| 2008/0300651 A1 * | 12/2008 | Gerber et al. | 607/41 |
| 2009/0062758 A1 | 3/2009 | Ales, III et al. | |
| 2009/0083240 A1 | 3/2009 | Nolan et al. | |
| 2009/0326417 A1 | 12/2009 | Ales, III et al. | |
| 2009/0326491 A1 | 12/2009 | Long et al. | |
| 2010/0009713 A1 | 1/2010 | Freer | |
| 2010/0017265 A1 * | 1/2010 | Weingarten | G06Q 30/02 705/7.29 |
| 2010/0076254 A1 | 3/2010 | Jimenez et al. | |
| 2010/0098341 A1 | 4/2010 | Ju et al. | |
| 2010/0111383 A1 * | 5/2010 | Boushey | G06K 9/00 382/128 |
| 2010/0114046 A1 | 5/2010 | Ales et al. | |
| 2010/0168700 A1 | 7/2010 | Schmidt et al. | |
| 2010/0201524 A1 | 8/2010 | Gallagher | |
| 2010/0211897 A1 * | 8/2010 | Cohen | G06Q 50/22 715/764 |
| 2010/0268552 A1 | 10/2010 | Schoenberg et al. | |
| 2010/0298803 A1 * | 11/2010 | Popp | A61F 13/55115 604/385.23 |
| 2011/0015496 A1 | 1/2011 | Sherman et al. | |
| 2011/0046571 A1 | 2/2011 | Waldhorn | |
| 2011/0063433 A1 | 3/2011 | Thonhauser | |
| 2011/0099027 A1 | 4/2011 | Weathers | |
| 2011/0125063 A1 | 5/2011 | Shalon et al. | |
| 2011/0183712 A1 | 7/2011 | Eckstein et al. | |
| 2011/0222774 A1 | 9/2011 | Hong et al. | |
| 2011/0243425 A1 * | 10/2011 | Maltbie | G06K 9/00201 382/154 |
| 2011/0263952 A1 | 10/2011 | Bergman et al. | |
| 2012/0035496 A1 | 2/2012 | Denison et al. | |
| 2012/0040655 A1 | 2/2012 | Larkin | |
| 2012/0110725 A1 | 5/2012 | Lee | |
| 2012/0144403 A1 | 6/2012 | Hacigumus et al. | |
| 2012/0157948 A1 | 6/2012 | Nhan et al. | |
| 2012/0161960 A1 | 6/2012 | Cheng et al. | |
| 2012/0220969 A1 | 8/2012 | Jang et al. | |
| 2012/0239699 A1 | 9/2012 | Anand et al. | |
| 2012/0256750 A1 | 10/2012 | Novak | |
| 2012/0268278 A1 * | 10/2012 | Lewis | A61F 13/42 340/573.5 |
| 2012/0312086 A1 | 12/2012 | Paz et al. | |
| 2013/0018231 A1 | 1/2013 | Hong et al. | |
| 2013/0023786 A1 | 1/2013 | Mani et al. | |
| 2013/0024873 A1 | 1/2013 | Hillier | |
| 2013/0046239 A1 | 2/2013 | Gonnelli et al. | |
| 2013/0110063 A1 | 5/2013 | Abraham et al. | |
| 2013/0110064 A1 * | 5/2013 | Richardson et al. | 604/361 |
| 2013/0303867 A1 | 11/2013 | Elfstrom et al. | |
| 2014/0121487 A1 * | 5/2014 | Faybishenko | A01K 23/00 600/365 |
| 2014/0301628 A1 | 10/2014 | Carney | |
| 2014/0327546 A1 * | 11/2014 | Carney | A61F 13/42 340/573.5 |
| 2014/0333442 A1 | 11/2014 | Carney | |
| 2014/0372177 A1 * | 12/2014 | Agami | G06Q 30/0201 705/7.32 |
| 2015/0148623 A1 * | 5/2015 | Benaron | A61B 5/0059 600/306 |
| 2015/0168365 A1 * | 6/2015 | Connor | G01N 33/02 356/51 |
| 2015/0223755 A1 | 8/2015 | Abir | |
| 2015/0330958 A1 | 11/2015 | Carney et al. | |
| 2016/0095758 A1 * | 4/2016 | Haire | A61F 13/42 600/301 |
| 2016/0095764 A1 * | 4/2016 | Seitz | A61F 13/5511 604/368 |
| 2016/0175164 A1 * | 6/2016 | Mashin-Chi | G06F 19/3481 705/2 |

FOREIGN PATENT DOCUMENTS

| | | |
|---|---|---|
| DE | 103 26 489 A1 | 1/2005 |
| DE | 10 2006 053 405 A1 | 5/2008 |
| DE | 10 2009 054 097 A1 | 5/2011 |
| EP | 2 175 398 A1 | 4/2010 |
| JP | H10-234761 A | 9/1998 |
| JP | 2000-245779 A | 9/2000 |
| JP | 2000-333989 A | 12/2000 |
| JP | 2001-161732 A | 6/2001 |
| JP | 2001-314433 A | 11/2001 |
| JP | 2002-073805 A | 3/2002 |
| JP | 2002-107361 A | 4/2002 |
| JP | 2002-113008 A | 4/2002 |
| JP | 2003-111797 A | 4/2003 |
| JP | 2003-126140 A | 5/2003 |
| JP | 2003-141256 A | 5/2003 |
| JP | 2004-503014 A | 1/2004 |
| JP | 2004-212060 A | 7/2004 |
| JP | 2004-531287 A | 10/2004 |
| JP | 2005-087543 A | 4/2005 |
| JP | 2006-303898 A | 11/2006 |

(56) References Cited

FOREIGN PATENT DOCUMENTS

| | | |
|---|---|---|
| JP | 2007-167264 A | 7/2007 |
| JP | 2008-217724 A | 9/2008 |
| JP | 2008-264232 A | 11/2008 |
| JP | 2012-105839 A | 6/2012 |
| RU | 2435181 C2 | 11/2011 |
| WO | WO 01/50996 A1 | 7/2001 |
| WO | 02/03902 A2 | 1/2002 |
| WO | 02/34127 A1 | 5/2002 |
| WO | 02/100292 A2 | 12/2002 |
| WO | 2007/128038 A1 | 11/2007 |
| WO | WO 2007128038 A1 * | 11/2007 |
| WO | WO 2008/023289 A1 | 2/2008 |
| WO | WO 2008/038167 A2 | 4/2008 |
| WO | 2008/055991 A2 | 5/2008 |
| WO | WO 2008/147612 A1 | 12/2008 |
| WO | WO 2009/027871 A1 | 3/2009 |
| WO | WO 2010/040430 A1 | 4/2010 |
| WO | WO 2011/008838 A1 | 1/2011 |
| WO | WO 2011/054045 A1 | 5/2011 |
| WO | WO 2011/057723 A1 | 5/2011 |
| WO | WO 2011/080639 A1 | 7/2011 |
| WO | 2011/125003 A1 | 10/2011 |
| WO | WO 2011/126497 A1 | 10/2011 |
| WO | WO 2011/162402 A1 | 12/2011 |

OTHER PUBLICATIONS

UroToday Bladder Diary App.*
Office Action (Notification of the First Office Action) dated Jan. 6, 2015, by the State Intellectual Property Office (SIPO) of the People's Republic of China in Chinese Patent Application No. 201180075757.1, and an English Translation of the Office Action. (20 pages).
International Preliminary Report on Patentability (Form PCT/IB/373) with accompanying Written Opinion of the International Searching Authority (Form PCT/IB/237), dated Jun. 24, 2014 in PCT/SE2011/051566, 8 pages, The International Bureau of WIPO, Geneva, CH.
Carney, Joshua, U.S. Appl. No. 14/360,774, entitled "Method for Measuring the Absorption of Fluid in an Abosrbent Product," filed in U.S. Patent and Trademark Office May 27, 2014.
Carney, Joshua, U.S. Appl. No. 14/362,261, entitled "Method, Monitoring System and Computer Program for Monitoring Use of an Absorbent Product," filed in U.S. Patent and Trademark Office on Jun. 2, 2014.
Carney, Joshua, U.S. Appl. No. 14/363,313, entitled "Method and Computer Program for Monitoring Use of an Absorbent Product," filed in U.S. Patent and Trandemark Office on Jun. 6, 2014.
Extended European Search Report dated Oct. 14, 2014, by the European Patent Office in corresponding European Patent Application No. 118781541-1952 / 2793785 (9 pgs).
Wai et al., "Smart Phone Reminder System for Managing Incontinence at Nursing Home", Consumer Electronics (ISCE), 2011 IEEE 15th International Symposium on Consumer Electronics, Jun. 14, 2011, pp. 254-259, XP032007856, Singapore.
International Search Report (Form PCT/ISA/210) dated Sep. 14, 2012, by the Swedish Patent Office in International Application No. PCT/SE2011/051565. (5 pages).
International Search Report (Form PCT/ISA/210) dated Sep. 18, 2012, by the Swedish Patent Office in International Application No. PCT/SE2011/051558. (5 pages).
Notification of Transmittal of the International Preliminary Report on Patentability (Forms PCT/IPEA/409 and PCT/Separate Sheet/409) dated Apr. 28, 2014, by the European Patent Office in International Application No. PCT/SE2011/051558. (6 pages).
Communication in cases for which no other form is applicable (Form PCT/IPEA/424) and Corrected International Preliminary Report on Patentability (Forms PCT/IPEA/409 and PCT/Separate Sheet/409) with Annex pages, dated May 27, 2014, by the European Patent Office in International Application No. PCT/SE2011/051558. (13 pages).
International Search Report (Form PCT/ISA/210) dated Sep. 18, 2012, by the Swedish Patent Office in International Application No. PCT/SE2011/051551. (5 pages).
Notification of Transmittal of the International Preliminary Report on Patentability (Forms PCT/IPEA/416, PCT/IPEA/409 and PCT/Separate Sheet/409) dated Jun. 2, 2014, by the European Patent Office in International Application No. PCT/SE2011/051551. (10 pages).
The extended European Search Report dated Mar. 4, 2015, by the European Patent Office in corresponding European Patent Application No. 11878058.4-1906. (4 pages).
International Search Report (PCT/ISA/210) dated Sep. 18, 2012, by the Swedish Patent Office as the International Searching Authority for International Application No. PCT/SE2011/051566.
Office Action issued by the U.S. Patent and Trademark Office in the U.S. Appl. No. 14/363,313, dated May 21, 2015, U.S. Patent and Trademark Office, Alexandria, VA. (33 pages).
Office Action issued by the U.S. Patent and Trademark Office in the U.S. Appl. No. 14/362,261, dated May 12, 2015, U.S. Patent and Trademark Office, Alexandria, VA, (26 pages).
Office Action (Patent Examination Report No. 1) dated Apr. 17, 2015 by the Australian Intellectual Property Office in corresponding Australian Patent Application No. 2011383785. (3 pages).
International Search Report (PCT/ISA/210) dated Jul. 4, 2013, by the Swedish Patent Office as the International Searching Authority for International Application No. PCT/SE2012/050910. (5 pages).
Written Opinion (PCT/ISA/237) dated Jul. 4, 2013, by the Swedish Patent Office as the International Searching Authority for International Application No. PCT/SE2012/050910. (9 pages).
Written Opinion of the International Preliminary Examining Authority (PCT/IPEA/408) dated Aug. 22, 2014, by the European Patent Office as the International Preliminary Examining Authority for International Application No. PCT/SE2012/050910. (7 pages).
International Preliminary Report on Patentability/Annex-Amended Sheets, issued in PCT/SE2012/050910, dated Jan. 28, 2015, European Patent Office, Berlin, DE (16 pages).
Carney, Joshua, et al., U.S. Appl. No. 14/424,350 entitled "Method and Mobile Applications using Cross-Sharing Database for Monitoring Use of Hygiene Products," filed in the U.S. Patent and Trandemark Office on Feb. 26, 2015.
Notice of Allowance and Fee(s) due issued by the U.S. Patent and Trademark Office in the U.S. Appl. No. 14/360,774, dated Sep. 30, 2015, U.S. Patent and Trademark Office, Alexandria, VA. (11 pages).
An English Translation of the Office Action (Notice of Reasons for Rejection) dated Jul. 27, 2015, by the Japan Patent Office in Japanese Patent Application No. 2014-548726. (4 pages).
An English Translation of the Office Action (Notice of Reasons for Rejection) dated Aug. 10, 2015, by the Japanese Patent Office in Japanese Patent Application No. 2014-548727. (3 pages).
An English Translation of the Office Action (Notice of Reasons for Rejection) dated Aug. 10, 2015, by the Japanese Patent Office in corresponding Japanese Patent Application No. 2014-548729. (5 pages).
Office Action issued by the U.S. Patent and Trademark Office in U.S. Appl. No. 14/360,774, dated Jul. 7, 2015, U.S. Patent and Trademark Office, Alexandria, VA. (24 pages).
An Examination Report dated Oct. 23, 2015, by the Canadian Patent Office in Canadian Patent Application No. 2,857,627. (5 pages).
Final Office Action issued by the U.S. Patent and Trademark Office in U.S. Appl. No. 14/363,313, dated Nov. 5, 2015, U.S. Patent and Trademark Office, Alexandria, VA. (26 pages).
Final Office Action issued by the U.S. Patent and Trademark Office in U.S. Appl. No. 14/362,261, dated Nov. 13, 2015, U.S. Patent and Trademark Office, Alexandria, VA. (24 pages).
Office Action (Decision on Grant) dated Jan. 26, 2016, by the Russian Patent Office in Russian Patent Application No. 2015111253/12(017533) and an English Translation of the Office Action. (16 pages).
Office Action dated May 20, 2016, by the U.S. Patent and Trademark Office in U.S. Appl. No. 14/362,261 (19 pages).

(56) References Cited

OTHER PUBLICATIONS

English translation of Notice of Reasons for Rejection dated May 30, 2016, by the Japanese Patent Office in corresponding Japanese Patent Application No. 2015-529750 (4 pages).
Office Action dated Nov. 3, 2016, by the U.S. Patent and Trademark Office in U.S. Appl. No. 14/362,261. (28 pages).
Notice of Allowance dated Apr. 22, 2016, by the U.S. Patent and Trademark Office in U.S. Appl. No. 14/363,313. (5 pages).
Final Office Action dated Sep. 18, 2017 by the U.S. Patent and Trademark Office in U.S. Appl. No. 14/362,261. (28 pages).
Office Action dated Mar. 31, 2017, by the U.S. Patent and Trademark Office in U.S. Appl. No. 14/362,261. (25 pages).
Office Action dated Nov. 28, 2017, by the U.S. Patent and Trademark Office in U.S. Appl. No. 14/424,350. (63 pages).
European Communication pursuant to Article 94(3) dated Oct. 10, 2017 by the European Patent Office in European Patent Application No. 11 878 017.0. (4 pages).
Office Action dated Nov. 1, 2017, by the Canadian Intellectual Property Office in corresponding Canadian Patent Application No. 2,859,144. (6 pages).

\* cited by examiner

METHOD AND COMPUTER PROGRAM FOR MONITORING USE OF AN ABSORBENT PRODUCT

TECHNICAL FIELD

The present disclosure relates to a method for monitoring use of an absorbent article, a mobile device for carrying out the method, and a computer program for causing the mobile device to carry out the method.

BACKGROUND

Urinary and/or faecal incontinence causes many people to use various types of absorbent products, such as incontinence pads, diapers etc.

Monitoring and timely change of absorbent products may sometimes be difficult, not only when it comes to babies wearing diapers but also when it comes to adults who due to the inability to control the urinary or faecal function find it difficult to know when voiding has taken place and hence when to change the absorbent product. This problem may also concern people suffering from physical or mental disorders preventing proper monitoring and change of absorbent products. The problem of properly monitoring and timely changing absorbent products is often most apparent during night when the wearer of the product is asleep.

Improper monitoring and change of absorbent products may cause urinary and faecal leakage from the product. To many people suffering from incontinence, this is a huge problem often causing feelings of shame and humiliation and sometimes even social withdrawal and isolation.

Several solutions for improved monitoring of use of absorbent articles are known from prior art.

US 2007/0252713 discloses an absorbent sensor pad worn by a patient. One or more sensors that measure urinary voiding parameters are integrally formed in the pad. The sensors may include impedance sensors, strain gauges, temperature sensors, accelerometers, pH sensors, and chemical sensors that measure wetness, volume, temperature, pH, and contents of urine voided by a patient as well as the posture and activity of the patient. The voiding data sensed by the sensors may be stored in a voiding log which may be transmitted to an external device connected to the sensors.

US 2009/0062758 relates to a wetness monitoring system for e.g. a diaper. The system includes a wetness sensor capable of counting the number of discrete insults, and an alarm that is triggered after a critical number of insults, or when a certain period of time has elapsed since the last change of product.

US 2011/0263952 discloses an incontinence management system for monitoring wetness in absorbent articles. The system comprises input for receiving sensor signals indicative of a presence of wetness in an absorbent article and a user interface for communicating with a user of the system.

However, known solutions for monitoring use of absorbent articles often involve complex and expensive products and/or monitoring systems that are not readily available to the public.

SUMMARY

It is an object of the present disclosure to solve or at least mitigate one or more of the above mentioned problems.

In particular, it is an object of the present disclosure to provide a cost efficient and readily available method for monitoring use of absorbent products.

Another object of the present disclosure is to provide a method that can help preventing too late change of absorbent products.

These and other objects are achieved by a method for monitoring use of an absorbent product, such as an incontinence pad or a diaper, worn by a wearer. The method comprises the steps of:

obtaining, by means of a mobile device, intake information indicative of intake of fluid and/or solid edible material by the wearer, obtaining, by means of the mobile device, voiding information indicative of urinary and/or faecal voiding by the wearer, predicting, based on the intake and voiding information, future voiding by the wearer, and providing, by means of the mobile device, product-related information based on said prediction to the wearer or a caregiver of the wearer.

The present disclosure hence relies on the features of predicting a future voiding behaviour based on at least intake and voiding information, and providing recommendations as to the use of the absorbent product based on said prediction. The present disclosure makes use of the findings that daily intake of fluid and solid edible material and urinary and faecal behaviour of the user can be used to predict future voiding behaviour. By registering or by other means obtaining information relating to the daily intake and voiding behaviour of the wearer, product-related information that facilitates the use of the absorbent product can be derived and provided to the wearer or a caregiver of the wearer. For example, the product-related information may comprise a recommendation to change the absorbent product before a certain time, displayed on the mobile device, or another communication device with which the mobile device can communicate.

The use of a mobile device, such as a mobile phone, a personal digital assistant (PDA), a tablet computer or any other hand-held computing device, makes the method readily available to anyone in possession of such a mobile device. The method is performed by the mobile device through execution of a computer program, which, in a preferred embodiment, is realised in form of an App that is downloadable to a storage medium of the mobile device. By allowing the method to be performed through execution of an App that may be downloaded into existing mobile devices, the method truly becomes readily available to anyone.

Product-related information herein means information related to the use of the absorbent product. The product-related information may comprise any of or any combination of:

an indication that no change of product is necessary,
a recommendation to change the product,
a recommendation to change the product before a certain time,
a recommendation to exchange the product for another absorbent product having higher or lower capacity than the currently worn product.

The content of the product-related information and additionally also the way the product-related information is provided to the user is determined by the mobile device based on the prediction of future voiding.

The intake information on which the prediction of future voiding is based may comprise information relating to at least one and preferably a plurality of intakes of fluid and/or solid edible material by the product-wearer.

For each intake, the intake information may comprise a time indication indicating when the intake was made. The time indication may be an indication of the actual time of the intake or an indication of whether the intake was made during breakfast, lunch, dinner, etc. Furthermore, for each intake, the intake information may comprise a type indication indicating the type of the intake. The intake may be any type of intake, including but not limited to intake of liquid, (solid) food, or liquid or solid medicaments. Yet further, for each intake, the intake information may comprise an amount indication indicating the amount or size of the intake. The amount indication may be an indication of the actual volume or weight of the intake or it may be an indication of whether the intake was small, average or big in size.

Likewise, the voiding information on which the prediction of future voiding is based may comprise information relating to at least one and preferably a plurality of urinary and/or faecal insults.

For each insult, the voiding information may comprise at least a time indication indicating when the insult occurred. The time indication is preferably a parameter indicating the actual time of the insult. Furthermore, for each insult, the voiding information preferably comprises a type indication indicating the type of the insult, e.g. whether the insult was a urinary or faecal insult. Yet further, for each insult, the voiding information may comprise an amount indication indicating the amount urine or faeces voided. The amount indication may be a parameter indicating an estimated or measured volume and/or weight of urine or faeces voided, or a parameter indicating whether the insult was small, average or big in size.

The intake and voiding information is preferably obtained by the mobile device by having the product-wearer or his caregiver enter the information manually on the mobile device. In a preferred embodiment of the present disclosure, the intake and voiding information is obtained from manual input of information on the mobile device relating to actual intakes and insults by the product-wearer. Preferably, this information is obtained by letting the product-wearer keep a daily digital log on the mobile device, wherein daily intakes of fluid and/or solid edible material as well as daily insults of urine and/or faeces are registered by the product-wearer and used by the mobile phone to predict future voiding.

Preferably, the method further comprises a step of obtaining capacity information related to the capacity of the absorbent product. The product-related information may then be provided based on both the prediction of future voiding by the wearer and said capacity information. By providing the product-related information based on both the prediction and the capacity information, the product related information can be based on a relation between future urinary and/or faecal voiding of the product-wearer and the capacity of the product, which allows the product-related information to comprise well-founded recommendations as to the need of changing the product.

Preferably, the method comprises the steps of:
determining a first parameter indicative of the amount of urine and/or faeces that can be absorbed by the absorbent product based on said capacity information,
determining a second parameter indicative of a predicted amount of urine and/or faeces voided by the wearer at a future point in time based on the predicted future voiding,
comparing said first and said second parameter, and
providing the product-related information based on said comparison.

In this way, a future point in time at which the predicted amount voided by the wearer exceeds the amount that can be absorbed by the product can be established, and product-related information comprising a recommendation to change the absorbent product before said point in time can be provided to the wearer.

According to one embodiment of the present disclosure, the mobile device is configured to determine a maximum number of insults of urine and/or faeces that can be absorbed and/or retained by the absorbent product, based on the capacity information. In this embodiment, the prediction of future voiding involves prediction of discrete future insults of urine and/or faeces by the wearer. The product-related information to be provided to the wearer may then be selected by the mobile device based on a comparison between said maximum number of insults and a predicted number of future insults by the wearer.

As indicated above, the method may be a computer-implemented method performed by a mobile device through execution of a computer program. Thus, according to another aspect of the present disclosure there is provided a computer program for monitoring use of an absorbent product worn by a wearer. The computer program is configured to cause a mobile device to perform the method when executed by a processor of the mobile device.

The present disclosure also provides a computer program product comprising a non-volatile memory for storing computer-readable instructions, wherein the above mentioned computer program is encoded on said non-volatile memory.

Furthermore, the present disclosure provides a mobile device for monitoring use of an absorbent product worn by a wearer. The mobile device comprises a processor and a storage medium for storing computer programs executable by said processor, which storage medium stores the above mentioned computer program.

DETAILED DESCRIPTION

Figure 1:
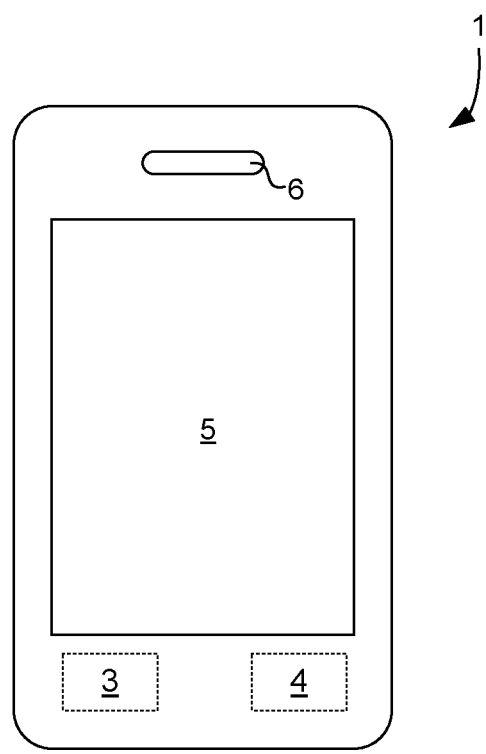
FIG. 1 illustrates a mobile device operable to perform a method according to one embodiment through execution of a computer program.

FIG. 1 illustrates a mobile device 1 for performing the method according to one embodiment. The mobile device 1 in FIG. 1 is a mobile phone in form of what is often referred to as a smartphone but it should be appreciated that the mobile device according to the embodiment may be any type of hand-held computing device, such as a personal digital assistant (PDA) or a tablet computer, devised and configured as set forth below.

The mobile device 1 comprises a processor 3 for processing data. The data may be received from communication devices to which the mobile device 1 is communicatively connectable via a network, or stored on a digital storage medium 4 of the mobile device, which storage medium is accessible by the processor 3.

The mobile device 1 is further seen to comprise a display 5 for displaying information to a user, and, if realised in form of a touch-display, also for receiving information from the user in form of user input. The mobile device 1 may also comprise other means for receiving user input, such as buttons, microphones, etc. Furthermore, the mobile device 1 comprises a loudspeaker 6 for outputting sound signals to the user.

The mobile device 1 is operable to perform all method steps of the inventive method, which method steps will be described in more detail below, through execution of a computer program stored in the storage medium 4.

Preferably, the computer program is realised in form of a stand-alone application, meaning that no data has to be received from application servers residing on a network to which the mobile device 1 is connected. However, the computer program may also be a client application of a distributed software solution further comprising a server-side application residing in an application server to which the mobile device is communicatively connectable. In this case, some of the method steps described below may be performed by the application server through execution of the server-side application.

In a preferred embodiment, the computer program stored on the mobile device 1 is realised in form of an App. An App, sometimes referred to as a mobile app or a mobile application, is a software application specifically designed to run on mobile devices such as smartphones and tablet computers. The App is downloadable into the storage medium 4 from a download server to which the mobile device 1 is connectable. The App may be adapted to a particular mobile operating system, such as Apple iOS, Google Android or Blackberry OS and distributed through known application distribution platforms.

It should thus be appreciated that "the App" hereinafter refers to the computer program stored on the storage medium 4 of the mobile device 1. The App can be executed by means of touching a particular icon displayed on the display 5 of the mobile device 1.

The absorbent product referred to herein is an absorbent personal hygiene article, including but not limited to male or female incontinence protectors, sanitary pads, diapers with tape fastener, pant diapers and belted diapers. The person wearing the absorbent product is herein referred to as the wearer or the product-wearer.

Figure 2:
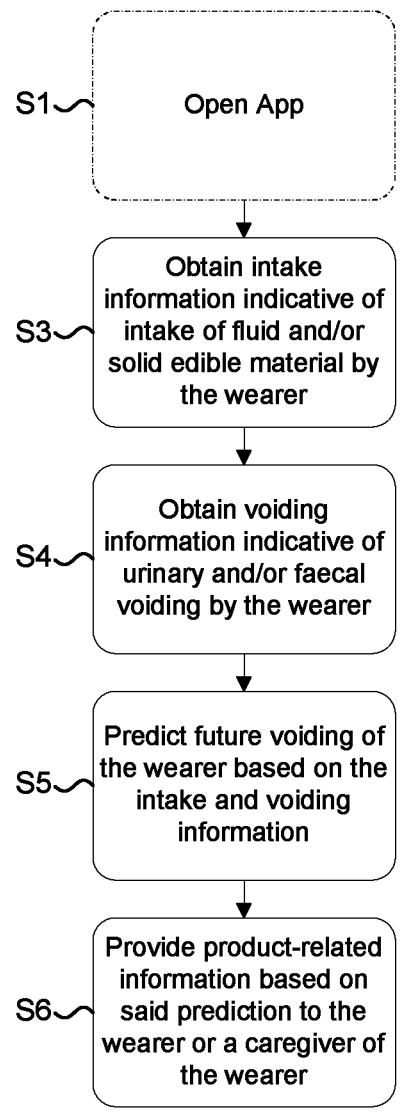
FIG. 2 is a flow chart illustrating the basic principles of the method according to one embodiment.
Figure 3:
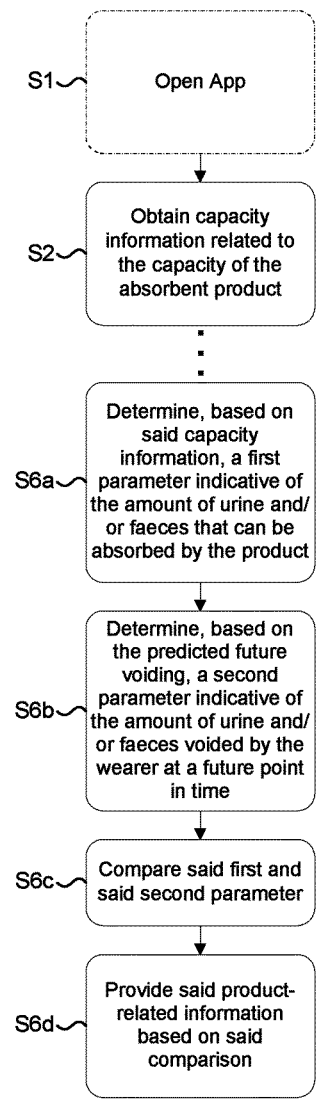
FIG. 3 is a flow chart illustrating a refined embodiment of the method according to one embodiment.

FIGS. 2 and 3 are flowcharts illustrating different aspects of the inventive method for monitoring use of an absorbent product. In the description of these flowcharts, simultaneous reference will be made to the mobile device 1 in FIG. 1.

In the flowcharts of FIGS. 2 to 3, boxes drawn with dashed lines indicate method steps performed by a user of the App, e.g. the product-wearer, while boxes drawn with continuous lines indicate method steps performed by the mobile device 1 through execution of the App.

FIG. 2 illustrates the basic principles of the inventive method.

In step S1, the App is opened in order to be able to perform said method.

In step S3, intake information indicative of intake of fluid and/or solid edible material by the wearer is obtained by means of the mobile device 1. The intake information may comprise information relating to one or more actual intakes of fluid and/or solid edible material by the product-wearer, and/or information that is derived statistically by the mobile device 1 based on known information about the product-wearer.

In step S4, voiding information indicative of urinary and/or faecal voiding of the wearer is obtained by means of the mobile device 1. The voiding information may comprise information relating to one or more actual insults of urine and/or faeces by the product-wearer, and/or information that is derived statistically by the mobile device 1 based on known information about the product-wearer.

In step S5, future voiding of the wearer is predicted based on the intake and voiding information obtained in the steps S3 and S4. The prediction may involve prediction of the time for future insults of urine and/or faeces. It may further involve prediction of the type of future insults, i.e. whether the future insults are likely to be urinary insults or faecal insults. Yet further, it may involve prediction of the amount of urine and/or faeces of future insults.

In a sixth step S6, product-related information related to the use of the absorbent product is provided based on said prediction. That the product-related information is provided based on the prediction means that at least the content of the product-related information is based on the prediction. Preferably, also the way the product-related information is provided to the wearer or the caregiver is based on the prediction. The product-related information is preferably provided to the product-wearer through visual, audible and/or vibratory signalling on the mobile device 1. Instead, or in addition, it may be provided on a communication device, such as another mobile device or a computer, with which the mobile device can communicate, for example a communication device of a caregiver of the product-wearer. In the latter scenario, the product-related information may be provided to the communication device e.g. in form of a text message (sms) or an e-mail.

Preferably, the intake and voiding information is obtained by the mobile device 1 by letting the product-wearer keep a daily digital log on the mobile device, wherein daily intakes of fluid and/or solid edible material as well as daily insults of urine and/or faeces are registered by the product-wearer. To this end, the App preferably comprises a user interface comprising information-collection means to which the intake and voiding information can be entered by the product-wearer. The information-collection means may comprise text fields, drop-down menus, option buttons etc. Preferably, the information-collection means are configured to allow the product-wearer to input intake information comprising information related to the time of the intake, the size of the intake (e.g. a volume or weight of the) and the type of the intake (e.g. fluid or solid). Similarly, the information-collection means are preferably configured to allow the product-wearer to input voiding information comprising information related to the time of urinary and/or faecal insults, the size of the insult (e.g. a volume or weight of urine and/or faeces voided) and the type of the insult (e.g. urinary or faecal insult). The App is preferably configured to store the intake and voiding information in a database of the mobile device 1.

In other embodiments, the intake and/or the voiding information may, at least to some extent, be automatically obtained by the mobile device 1 based on information about the product-wearer. In this case the method may comprise the step of presenting, on the mobile, device, one or more questions about to the product-wearer, and to derive the intake and/or voiding information based on the answers to said questions. In addition to the information about the product-wearer, known statistical data on intake and/or voiding behaviour may be used to derive the intake and/or voiding information. The questions may relate to the product-wearer's normal intake routines and/or the product-wearer's normal voiding behaviour. They may also relate to the product-wearer himself and/or the health of the product-wearer. For example, the questions may include questions about when the product-wearer normally eats, drinks, urinates and defecates, and/or questions about the product wearer's age, gender, health, use of medicaments, etc. Information relating to the product-wearer's potential use of drugs for treatment of incontinence (e.g. the type and/or dosage of the drug) is of particular interest and may be used by the App to obtain relevant voiding information. The obtained information about the product-wearer can then be used to estimate the intake and/or the voiding information.

In other embodiments, the intake and/or the voiding information may be obtained automatically by the mobile device 1. For example, the mobile device may be configured to identify a food or liquid product automatically by means of a camera and suitable image recognition software, an RFID reader or a barcode scanner of the mobile device, and to obtain at least some of the intake information automatically from a product database stored on the mobile device 1 or an application server with which the mobile device can communicate. To this end, the absorbent product may be provided with means for facilitating automatic identification thereof, such as a barcode (e.g. a QR code) or an RFID tag. The voiding information may also be obtained automatically by the mobile device 1 through communication with an external insult monitoring device. An example of such an insult monitoring device is a wetness sensor arranged in the absorbent product and configured to communicate detection of urinary and/or faecal insults to the mobile device. Another example is an odour sensor configured to detect urinary and/or faecal insults through gas composition analysis and to communicate the detection of an insult to the mobile device.

The App further comprises logic for predicting the future voiding by the wearer based on the intake information and the voiding information. The logic typically comprises one or more prediction algorithms for predicting the future voiding, wherein the intake information and the voiding information are used by the App as input parameters to said prediction algorithms.

In a basic implementation, the App may be configured to use the time between a previously registered intake and a previously registered insult to predict the time to a future insult from the time of a newly registered intake. Preferably, the App is configured to use the times elapsed between a plurality of previously registered intakes and a plurality of previously registered insults to predict the time of future insults.

It should be understood, however, that the prediction does not have to be a prediction of the time to a future insult from the time of a newly registered intake. The App may be configured to predict also future intakes of fluid and/or solid edible material based on previously registered intake information, and to predict future voiding by the wearer also based on the predicted future intakes. If, for example, the product-wearer usually has an intake of food and liquid around 7 PM, the App may be configured to take this intake into account when predicting voiding likely to occur after 7 PM. For example, the App may already at 5 PM predict that the future intake at 7 PM will cause future voiding around 8 PM, and so display a recommendation on the mobile device 1 that the absorbent product should be changed before 8 PM.

To improve the accuracy of the prediction, the App is preferably configured to take the size of the registered intakes into account when predicting the future voiding of the product-wearer. As understood by person skilled in the art, mathematical statistics may be applied to the intake and voiding information in many different ways to predict the future voiding behaviour of the product-wearer.

The predictions may be used by the App in various ways. For example, the time at which a certain recommendation is provided to the product-wearer and/or a caregiver of the product-user may be adjusted based on the predicted time of the next insult. Moreover, the prediction can be used by the App to provide product-related information including a recommendation on when a future need for changing the product will arise. The product-related information may, depending on the prediction of future voiding of the product-wearer, comprise any of an indication that no change of product is necessary, a recommendation to change the product, a recommendation to change the product before a certain time, or a recommendation to exchange the product for another absorbent product having higher or lower capacity than the currently worn product.

FIG. 3 is a flow chart illustrating a refined embodiment of the method. In the following, only steps not described with reference to the flow chart in FIG. 2 are described.

In step S2, capacity information related to the capacity of the absorbent product is obtained.

The capacity information may comprise any of, or any combination of the type of the absorbent product, the absorbency level of the absorbent product, and the size of the absorbent product. The capacity information may be obtained from user input and/or reception of information from a server-side application residing on an application server with which the mobile device 1 can communicate.

In a preferred embodiment, step S2 of obtaining the capacity information comprises a first step of obtaining information about the type of the absorbent product, i.e. information telling the App whether the absorbent product is an incontinence pad, a diaper, etc. To this end, the App is preferably configured to display a list of several product types on the display of the mobile device 1, and to obtain the product type information by having the product-wearer indicating the correct alternative in the list of product types.

It may further comprise a second step in which the App obtains information about the absorbency level of the absorbent product. Many types of absorbent products, e.g. incontinence pads, are available within a wide range of absorbency levels, and the product's capability to absorb and retain liquid and/or faeces may vary substantially between different absorbency levels. Typically, the absorbency level is the level of the product's absorption capacity on a predefined scale, which level and scale are indicated on the package of the absorbent product. Preferably, the App is configured to display a scale of absorbency levels corresponding to a scale of absorbency levels presented on the package of the absorbency product, and to obtain the absorbency level by having the product-wearer indicating the correct absorbency level on the displayed scale.

The App may also be configured to obtain the capacity information automatically through automatic identification of the absorbent product. The App may be configured to identify the product automatically by means of a camera (and image recognition software), an RFID reader or a barcode scanner of the mobile device 1, and to obtain the capacity information automatically from a product database stored locally on the mobile device 1 or a product database stored on the above mentioned application server.

The sixth step, S6, in FIG. 2 is here seen to comprise four steps, S6a to S6d.

In step S6a a first parameter indicative of the amount of urine and/or faeces that can be absorbed by the product is determining based on said capacity information.

In some embodiments, the mobile device 1 may be configured to determine said first parameter as a maximum number of insults of urine and/or faeces that can be absorbed by the absorbent product. The first parameters may for example be determined as a maximum number of insults of urine that the absorbent product can absorb, determined based on user input indicating the type and the absorbency level of the absorbent product. For example, if the user has indicated that the absorbent product is a certain type of incontinence pad having an absorbency level 5 on a scale of 1 to 8, the App may use this information to determine that the product can absorb three insults of urine.

In other embodiments, the mobile device 1 may be configured to determine said first parameter as a maximum volume or weight of urine and/or faeces that can be absorbed by the absorbent product.

In yet other embodiments, the mobile device 2 is configured to retrieve the said first parameter from a database of the App itself or a database of a server-side application with which the App can communicate, using one or more parameters identifying the product type, the absorbency level of the product, and/or the size of the product as input parameters in the database request.

In step S6b a second parameter indicative of a predicted amount of urine and/or faeces voided by the wearer at a future point in time is determining based on the predicted future voiding.

In some embodiments, the App may be configured to determine said second parameter as a discrete number of insults of urine and/or faeces likely to have occurred at said future point in time.

In other embodiments, the mobile device 1 may be configured to determine said second parameter as volume or weight of urine and/or faeces likely to have been voided at said future point in time.

In step S6c, the first parameter and the second parameter are compared.

This comparison hence involves a comparison between a predicted amount of urine and/or faeces voided by the product-wearer at a future point in time, and the product's capacity to absorb urine and/or faeces. For example, it may involve a comparison between the number of predicted insults of urine at the future point in time and a maximum number of insults of urine that the absorbent product can absorb.

In step S6d, the product-related information is provided based on the result of the comparison in step S6c, meaning that at least the information content of the product-related information but preferably also the way the product-related information is provided is selected by the App based on the result of the comparison.

If the comparison in step S6c shows that the amount voided by the wearer at the future point in time is close to the capacity of the product, the product-related information can include a recommendation to change the product before that point time. If, however, the predicted amount voided by the wearer is well below the capacity of the product, the product-related information may comprise an indication that no change of product is required before that future point in time.

The comparison also allows the App to establish an actual point in time at which the predicted amount voided by the wearer will exceed the amount that can be absorbed by the product. The App can then provide product-related information to the product-wearer or a caregiver comprising a recommendation to change the absorbent product before said point in time, which information can be provided well before that point in time.

For some absorbent products, it may be desirable to distinguish between urinary and faecal insults by the product-wearer. If the absorbent product is a product for absorption of both urine and faeces, e.g. a diaper, the App may be configured to obtain capacity information indicative of the product's capacity to absorb and/or retain urine and faeces, respectively. With such a configuration, the App may be configured to receive voiding information indicative of both the amount of urine voided by the product-wearer and the amount of faeces voided by the product-wearer, and to predict an amount of urine voided by the wearer at a later point in time, and an amount of faeces voided by the wearer at a later point in time. The predicted amount of urine may then be compared with the product's capacity to absorb urine, and the predicted amount of faeces may be compared with the product's capacity to absorb and/or retain faeces, whereby the App may be configured to provide the product-related information based on any or both of said comparisons.

To further improve the accuracy in the prediction of future voiding, the App may be configured to allow the user to give feedback on the product-related information provided by the App, e.g. on recommendations on when to change the product. The process of obtaining user feedback may comprise the step of having the user answer to one or more questions before closing the App after use. For example, the App may be configured to display a question like "When where you recommended to change the product?" together with the reply options "too early", "in good time", and "too late", and to use the user feedback to adapt the prediction algorithms for predicting future voiding by the product-wearer.

The invention claimed is:

1. A method for monitoring a use of an absorbent product worn by a wearer, comprising at least the steps of:
   obtaining, by manually entering into a mobile device, capacity information related to a capacity of the absorbent product,
   obtaining, by manually entering into the mobile device, intake information indicative of intake of fluid and/or solid material by the wearer,
   obtaining, by manually entering into the mobile device, voiding information indicative of urinary and/or faecal voiding by the wearer,
   predicting, by the mobile device, based on the intake and voiding information, a future voiding by the wearer, wherein the mobile device is configured to determine a first parameter, based on said capacity information, indicative of a maximum volume or weight of said urinary and/or faecal voiding being absorbed by the absorbent product and determine a second parameter, based on said predicted future voiding, indicative of an amount of urinary and/or faecal voiding at a future point in time; and
   comparing, by the mobile device, the first parameter and the second parameter to provide product-related information to the wearer via a display of the mobile device,
   wherein said product-related information comprises a recommendation to change the absorbent product before a certain time, and a recommendation to exchange the absorbent product for another absorbent product having higher or lower capacity than the currently worn absorbent product,
   wherein the voiding information indicative of urinary and/or faecal voiding by the wearer is entered into the mobile device only manually, and
   wherein the absorbent, product is free of a sensor.

2. The method according to claim 1, wherein the intake information comprises information relating to one or more intakes of fluid and/or solid material by the wearer, and the voiding information comprises information relating to one or more urinary and/or faecal insults by the wearer.

3. The method according to claim 1, further comprises obtaining, by the mobile device, information about the wearer, wherein the information about the wearer comprises information selected from at east one of:
- normal intake routines of the wearer;
- normal voiding behaviour of the wearer;
- age of the wearer;
- gender of the wearer;
- health of the wearer, and
- use of medicines by the wearer.

4. The method according to claim 1, wherein the intake information comprises an indication of a point in time for one or more intakes, and the voiding information comprises an indication of a point in time for one or more insults of urine and/or faeces.

5. The method according to claim 1, wherein the intake information comprises an indication of an amount of one or more intakes of fluid and/or solid material.

6. The method according to claim 1, wherein the voiding information comprises an indication of an amount of one or more insults of urine and/or faeces.

7. The method according to claim 1, wherein the intake information comprises an indication of a type of the intake, and/or the voiding information comprises an indication of a type of voiding.

8. The method according to claim 1, wherein the capacity information comprises information selected from at least, one of:
- a type of the absorbent product,
- an absorbency level of the absorbent product, and
- a size of the absorbent product.

9. The method according to claim 1, wherein the product-related information further comprises a recommendation to change the absorbent product before a future point in time at which a predicted amount of urine and/or faeces exceeds an amount of urine and/or faeces that can be absorbed by the absorbent product.

10. The method according to claim 1, wherein the product-related information comprises a recommendation as to the use of the absorbent product.

11. The method according to claim 1, wherein said product-related information is further provided by at least one of audible, and vibratory signaling, on the mobile device.

12. The method according to claim 1, wherein the absorbent product is an absorbent personal hygiene article.

13. The method according to claim 12, wherein the absorbent personal hygiene article is one of a male or female incontinence protector, a sanitary pad, a diaper with tape fastener, a pant diaper and a belted diaper.

14. A non-transitory computer readable recording medium storing thereon a computer program for monitoring a use of an absorbent product worn by a wearer, wherein the computer program, when executed by a processor of a mobile device, causes the mobile device to perform the method according to claim 1.

15. A mobile device that monitors a use of an absorbent product worn by a wearer, the mobile device comprising a processor and a non-transitory computer readable recording medium storing thereon the computer program according to claim 14.

* * * * *